US007801266B2

(12) United States Patent
Nöttling et al.

(10) Patent No.: US 7,801,266 B2
(45) Date of Patent: Sep. 21, 2010

(54) METHOD FOR SPEEDING UP THE SCATTERED RADIATION CORRECTION IN A COMPUTED TOMOGRAPHY SYSTEM

(75) Inventors: Alois Nöttling, Pottenstein (DE);
Ernst-Peter Rührnschopf, Erlangen (DE); Bernhard Scholz, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 678 days.

(21) Appl. No.: 11/598,190

(22) Filed: Nov. 9, 2006

(65) Prior Publication Data
US 2007/0104310 A1 May 10, 2007

(30) Foreign Application Priority Data
Nov. 9, 2005 (DE) .................. 10 2005 053 498

(51) Int. Cl.
*A61B 6/03* (2006.01)
(52) U.S. Cl. ............................. 378/7; 378/18
(58) Field of Classification Search .............. 378/7, 378/18
See application file for complete search history.

(56) References Cited
U.S. PATENT DOCUMENTS 6,639,964 B2 * 10/2003 Schneider et al. .............. 378/7
6,687,326 B1 * 2/2004 Bechwati et al. .............. 378/7

FOREIGN PATENT DOCUMENTS

EP 1 566 771 A1 8/2005

OTHER PUBLICATIONS

Spies et al., Correction of scatter in megavoltage cone-beam CT, 2001, Physics in Medicine and Biology, vol. 46, pp. 821-833.*
Ay et al., Development and validation of MCNP4C-based Monte Carlo simulator for fan- and cone-beam x-ray CT, Oct. 5, 2005, Physics in Medicine and Biology, vol. 50, pp. 4863-4885.*
Kanamori et al., Effects of scattered x-rays on CT images, 1984, Physics in Medicine and Biology, vol. 30, No. 3, pp. 239-249.*
Hansen et al., Extraction of primary signal from EPIDs using only forward convolution, 1997, Medical Physics, vol. 24, No. 9, pp. 1477-1484.*
Feldkamp et al., Practical cone-beam algorithm, 1984, J. Opt. Soc. A, vol. 1, No. 1, pp. 612-619.*
Kak et al., Principles of Computerized Tomographic Imaging, 1988, IEEE Press, ISBN 0-87942-198-3.*
Siewerdsen et al., Cone-beam computed tomography with flat-panel imager: Magnitude and effects of x-ray scatter, 1985, Physics in Medicine and Biology, vol. 28, pp. 220-231.*

(Continued)

*Primary Examiner*—Edward J Glick
*Assistant Examiner*—John M Corbett (57) ABSTRACT

The invention relates to a method for speeding up the scattered radiation correction in a computed tomography system with a radiation source and a detector constructed in large-area format with a number of rows of detectors, by which an object is scanned from numerous projection angles, uses the measured values for the attenuation of the radiation in generating projection data which is postprocessed for the purpose of reconstructing tomographic views, in doing which a beam hardening correction is applied directly to the projection data, whereby according to the invention the scattered radiation correction is also applied directly to the projection data.

11 Claims, 3 Drawing Sheets

OTHER PUBLICATIONS

Cagnon, A Monte Carlo Based Simulation Tool for Modeling X-ray Computed Tomography Physics: Application to Electron Beam CT, 2003, Doctoral Dissertation, University of California at Los Angeles.*

Kijewski et al., Correction for beam hardening in computed tomography, 1978, Medical Physics, vol. 5, No. 3, pp. 209-214.*

M. Zellerhoff, B. Scholz, E.-P. Rührnschopf and T. Brunner, "Low contrast 3D-reconstruction from C-arm data", Proceedings of SPIE, Medical Imaging 2005, vol. 5745, Apr. 2005, pp. 646-655.

J.H. Siewerdsen, D. J. Moseley, B. Bakhtiar, S. Richard and D.A. Jaffray, "The influence of antiscatter grids on soft-tissue detectability in cone-beam computed tomography with flat-panel detectors", Med. Phys. 31 (12), Dec. 2004, pp. 3506-3520.

Ruola Ntng, Xiangyang Tang and D.L. Conover, "X-Ray Scatter Suppression Algorithm for Cone Beam Volume CT", Proceedings of SPIE vol. 4682, Medical Imaging 2002, Physics of Medical Imaging, Feb. 2002, pp. 774-781.

Harrison H. Barrett, "Radiological Imaging", The Theory of Image Formation, Detection, and Processing, vol. 2, Academic Press, 1981, pp. 438-441.

Avinash C. Kak and Malcolm Slaney, "Principles of Computerized Tomographic Imaging", IEEE Press New York, 1979, pp. 120-123, Internet: http://www.slaney.org/pct/pct-toc.html.

* cited by examiner

METHOD FOR SPEEDING UP THE SCATTERED RADIATION CORRECTION IN A COMPUTED TOMOGRAPHY SYSTEM

CROSS REFERENCE TO RELATED APPLICATIONS

This application claims priority of German application No. 10 2005 053 498.8 filed Nov. 9, 2005, which is incorporated by reference herein in its entirety.

FIELD OF THE INVENTION

The invention relates to a method for speeding up the scattered radiation correction in a computed tomography system with a radiation source and a large-area format detector with a number of rows of detectors, by which an object is scanned from numerous projection angles, the measured values for the attenuation of the radiation are used in generating projection data which is postprocessed for the purpose of reconstructing tomographic views, in doing which a beam hardening correction is applied directly to the projection data p.

BACKGROUND OF THE INVENTION

Computed tomography (CT) is a method by which it is possible to produce a 3-dimensional reconstruction of the distribution of tissue densities or, more precisely defined, a 3-dimensional distribution of the linear attenuation coefficients for X-ray irradiation of the interior of the body, with a high spatial resolution and a high quantitative precision in the resolution of the densities.

It is technically possible nowadays to map and reconstruct a large volume region with a short exposure time. To do so, use is made mainly of flat-panel detectors (FPD), using which even a single "half rotation", or more precisely a rotation through >180°+fan angle, enables informative CT views of limited volumes to be reconstructed by cone-beam computed tomography (CBCT). On the other hand, use is made of multi-row detectors, with multiple rotations around the patient and continuous advance, which can show the complete body of a patient tomographically by so-called spiral CT.

A serious problem is the scattered radiation produced in the exposed object, generally the patient, which increases with the area of the detectors and with the corresponding simultaneous increase in volume through which the radiation passes. Here, the intensity of the scattered radiation can reach the same order of magnitude as the unscattered direct primary radiation, and in extreme cases can indeed outweigh it. The consequence is a distortion in the quantitative reconstruction of the tissue thicknesses which, typically, in the case of a homogeneous cylindrical body for example, can be seen as a continuous darkening from the edge towards the center. This effect is called "cupping". This cupping can have a very detrimental effect on the ability to recognize small pathological structures with low contrast, since errors of a deviation of several 100 HU can arise between the edge of the object and its center. 1 HU (=Hounsfield Unit) corresponds to 1/1000 of the density of water.

With conventional CTs with single row or multi-row detectors, the scattered radiation is effectively suppressed by collimation. This is done, for example, by limiting the thickness of the exposed layer in the case of single row detectors, or the volume of the layer for multi-row detectors, by axial collimation towards the axis of rotation. Use can also be made of encapsulation, or collimation plates arranged between the sides of neighboring detector elements, as appropriate, that is lateral collimation.

In the case of flat-panel detectors, such as are mainly used in modern C-arm devices, the radiation is, not least on grounds of radiation protection, restricted by collimators to the measurement area—in general the detector area, in many applications even to just a part of the area. However, the scattered radiation which is produced in the patient cannot be suppressed by these measures. Otherwise, there is no possibility of lateral collimation at the flat-panel detector.

It is also possible to use antiscatter grids mounted in front of the detector input surface. Though their benefits for CBCT imaging are the subject of controversial discussions, as emerges from the paper by J. H. Siewerdsen, D. H Moseley, B. Bakhtiar, S. Richard, D. A. Jaffray: "*The influence of antiscatter grids on soft-tissue detectability in cone-beam computed tomography with flat-panel detectors*", Med. Phys. 31(12), December 2004, 3506 to 3520, their use is to be recommended at least when there is a large proportion of scattered radiation. In general however, the reduction in scattered radiation by antiscatter grids is insufficient, so that additional scattered radiation correction methods are necessary.

In the paper by R. Ning, X. Tang, D. L. Conover: "*X-ray scatter suppression algorithm for cone beam volume CT*", Proc. SPIE, Vol. 4682, 2002, 774 to 781, it was suggested that the scattered radiation should be measured and corrected in a few projection directions. For the measurement of the scattered radiation this requires that equipment is available with which a "beam-stop" carrier plate can be moved into the path of the radiation between the X-ray source and the patient, close to the patient. However, the additional measurement procedure thus required seems to be unacceptable in the normal clinical workflow.

In the paper by M. Zellerhoff, B. Scholz, E.-P. Rührnschopf, T. Brunner: "*Low contrast 3D reconstruction from C-arm data*", Proceedings of SPIE, Medical Imaging 2005, Vol. 5745, pages 646 to 655, a purely computational scattered radiation correction algorithm is suggested. This algorithm is indeed relatively fast, but the lengthening of the complete reconstruction time is not negligible. Thus, for 500 projection images with a size of 1024×1024 pixels, the algorithm still requires about 1 minute on a PC with a clock speed of 3 GHz.

SUMMARY OF THE INVENTION

From the point of view of clinical applications, in particular due to the increasing use of C-arm cone-beam CT systems with FPD in interventional medicine, there is a pressing requirement for the shortest possible computation time for volume reconstruction. Correction algorithms which are implemented as enhancements for improving the image quality will then only be accepted if they extend the computation time to a practically unnoticeable extent.

It is therefore the object of the invention to find a method for scattered radiation correction which requires low computational effort combined with resulting images which are essentially unchanged.

This objective is achieved by the characteristics of the main patent claims. Advantageous developments of the invention are the subject of the sub-claims.

The inventors have recognized that the effort required for the last-mentioned computational scattered radiation correction algorithm can largely be attributed to the operations of finding antilogarithms and logarithms in the correction step, required for each pixel value, in the correction step, and to a 2-dimensional convolution or image expansion, as applicable, within the scattered radiation estimation model used, and hence a correction method should be sought which does not use such demanding computational steps in the correction of each pixel.

Further, the inventors have realized that spectral beam hardening produces a very similar effect on the image as with scattered radiation. Although physically completely different in nature, it is practically impossible to distinguish between the cupping effects on the image arising for the two reasons. The hardening correction can be reduced to a simple "table-lookup" for each pixel in each projection image, and is therefore very fast.

The idea now consists in realizing the scattered radiation effect by a corresponding amplification of the hardening correction, and thereby to take advantage of the speed of the hardening correction. Such a scattered radiation correction could be achieved, so-to-speak, at "no cost" computationally. In particular, the demanding operations of taking antilogarithms and logarithms, and image expansion, would be eliminated.

In respect of the known methods for beam hardening correction, refer for example to the publications by H. H. Barrett, W. Swindell: Radiological Imaging, Vol. 2, Academic Press, 1981, pages 438 to 441, and by A. C. Kak, M. Slaney: Principles of Computerized Tomographic Imaging, IEEE Press New York, 1979, pages 120 to 123.

The main problem which remains is the determination of the scattered-radiation-dependent amplification factor. The data required for this purpose can be obtained, for example, in the same way as described in the publication cited above by M. Zellerhoff, B. Scholz, E.-P. Rührnschopf, T. Brunner: "*Low contrast 3D reconstruction from C-arm data*", Proceedings of SPIE, Medical Imaging 2005, Vol. 5745, pages 646 to 655. In doing this, use is made of a database which contains, for typical scattering bodies—water cylinders with an elliptical cross-section—the S/P ratios (intensity of the scattered radiation relative to the primary radiation) as a function of all the parameters which affect the scattered radiation, such as the thickness of the scattering body, air gap=distance from the scattering body to the detector, size of detector array, voltage of the X-ray tube, thickness and material of the prefilter on the X-ray side and the antiscatter grids. This database, stored in a multi-dimensional table, can be generated beforehand by demanding Monte-Carlo simulation calculations and reconciliation against measurements.

It should be remarked that the correction method, because it operates directly on the projection data, is independent of the exposure geometry, and in principle any reconstruction algorithm which is suitable for the exposure geometry can be used. However, this exposure geometry must be taken into account in generating the S/P database.

Corresponding to the basic idea outlined here, the inventors propose a method for speeding up the scattered radiation correction, in a computed tomography system with a radiation source and a large-area format detector with numerous detector rows, by which an object is scanned from numerous projection angles, the measured attenuation values $I_T/I_0$ for the radiation—where $I_T$ is the initial intensity and $I_0$ the measured intensity at the detector—are used to generate projection data $$p_T = \log \frac{I_T}{I_0}$$

which is postprocessed for the purpose of reconstructing tomographic views, in doing which a beam hardening correction is applied directly to the projection data items $p_T$. According to the invention, in doing this the scattered radiation correction is also applied directly to the projection data items $p_T$. This makes it possible to avoid the demanding computational operations of taking logarithms and antilogarithms, thus accelerating the overall speed of computation.

In a particularly preferred embodiment of the method, the inventors propose that for the purpose of scattered radiation correction a hardening correction term, which is already used for the beam hardening correction, is multiplied by an amplification factor for the purpose of scattered radiation correction.

A specific embodiment of the method could consist in using the amplification factor $\rho = 1 + 1/\delta_a \log(1+S/P_a)$ to calculate corrected projection data $p^* = p_T + \rho \cdot \delta_a$ for the combined hardening and scattered radiation correction, where $\delta_a$ specifies the correction term for the beam hardening correction, $S = I_S/I_0$ the standardized distribution of scattered radiation and $P_a = I_A/I_0$ the standardized primary radiation with hardening but without scattered radiation.

Here, the ratio $S/P_a$ of standardized scattered radiation S to the standardized primary radiation with hardening and without scattered radiation, $P_a$, can be estimated taking into account at least one representative pixel. Alternatively, the ratio $S/P_a$ can also be taken from simulation data for a phantom with a shape, size and structure similar to that of the object to be investigated. Another possibility consists in using an iterative method to approximate the ratio $S/P_a$.

It is furthermore advantageous if the amplification factor is determined as a function of the location, relative to the detector. In doing this, the amplification factor can also be determined as a function of the detector row under consideration.

In the case of objects which are not rotationally symmetric, at least in the region of the scan, the inventors also propose that the amplification factor be determined as a function also of the projection angle.

In accordance with a further particular embodiment of the method, the amplification factor can be multiplied in addition by a function, the value of which lies in a range between 0 and 1 and the value of which falls off to 0 at the edge of the object. Here, it is also advantageous if the function is raised to a power, so that the fall off in the value towards the edge of the object is steeper.

Also proposed is a CT system, corresponding to the method explained above, which is equipped with a radiation source and a large-area format detector having numerous rows of detectors, with which an object is scanned from numerous projection angles, whereby projection data is generated from the values measured for the attenuation of the radiation, and with a control and computation unit which has at least a memory for programs and data and which performs a reconstruction of tomographic views using stored programs and projection data. In accordance with the invention, in the CT system are stored computer programs or program modules which, in operation, perform the method steps of one of the preceding method claims.

BRIEF DESCRIPTION OF THE DRAWINGS

The invention is described in more detail below by reference to preferred exemplary embodiments, with the help of figures, in which only those characteristics required for an understanding of the invention are shown. For this purpose, the following reference marks are used: 1: CT system/C-arm device; 2: X-ray tube; 3: detector; 4: system axis; 5: gantry housing/C-arm; 6: patient table; 7: patient; 8: opening in the gantry housing; 9: control and computation unit; 10: memory; 11: ideal graph of the projection data with no scattered radiation or beam hardening; 12: graph of the projection data with scattered radiation and beam hardening; 13: graph of the projection data with no scattered radiation and with beam hardening; 14: graph of the beam hardening portion; 15: graph of the scattered radiation portion; 16: projection data corrected in accordance with the invention.

The individual figures show.

DETAILED DESCRIPTION OF THE INVENTION

Figure 1:
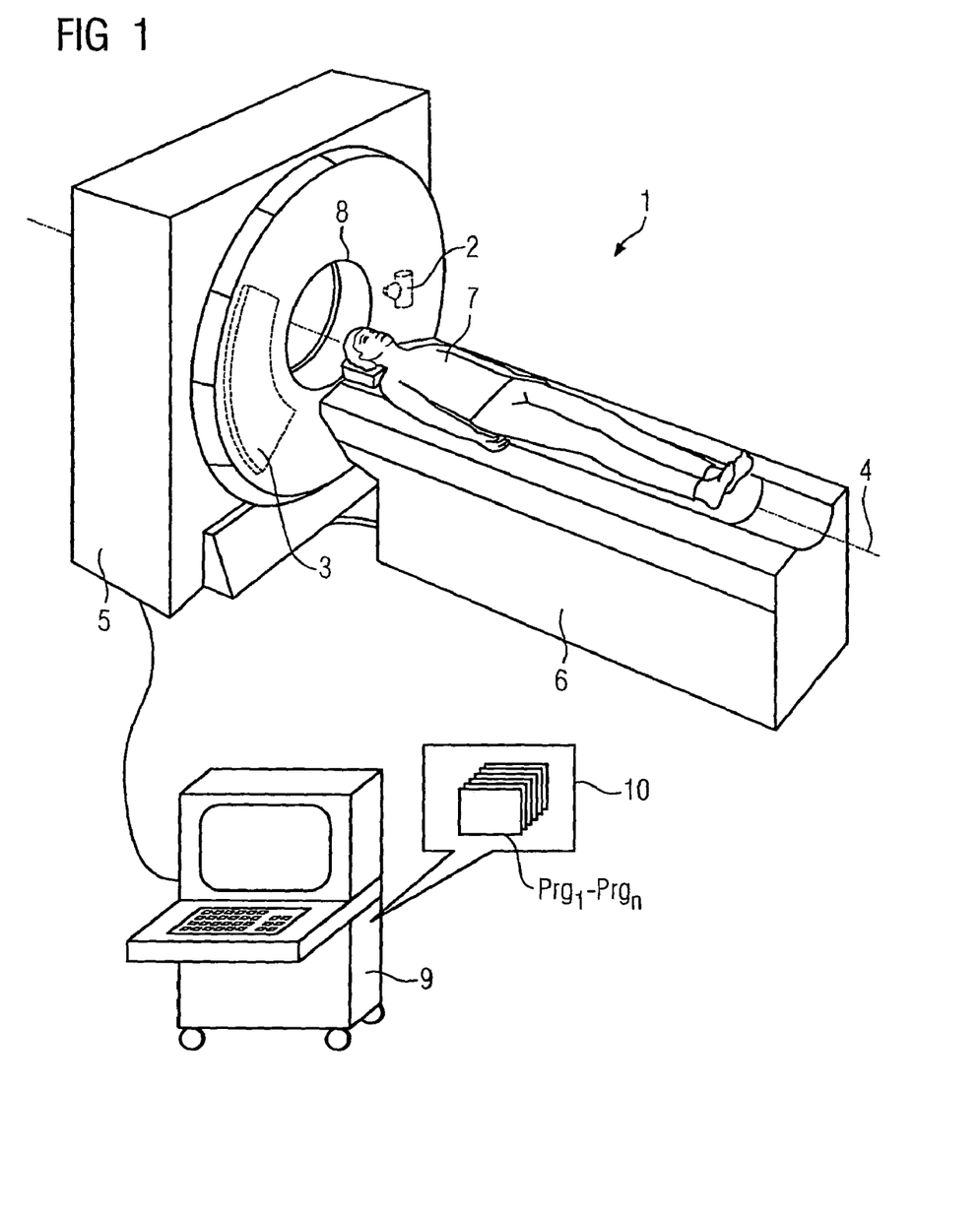
FIG. 1 a schematic diagram of a CT system with a gantry, for carrying out the method in accordance with the invention.

FIG. 1 shows a 3D view of a typical CT system 1 in accordance with the invention, which is suitable for performing the method in accordance with the invention. It consists in the familiar way of a gantry housing 5 in which is arranged the gantry, which here cannot be seen, to which are attached an X-ray tube 2 as the radiation source and a large-area multi-row detector 3. Lying on the patient table 6, the patient 7 to be scanned is pushed along the system axis 4 through the opening 8 in the gantry housing 5, continuously for a spiral scan or discontinuously for a circular scan, while the X-ray tube 2 attached to the gantry and the detector 3 lying opposite it rotate around the system axis 4. Control of the system is effected by a control and computation unit 9, which also has a memory 10 in which are stored the control and analysis programs $Prg_1$-$Prg_n$ of the CT system 1, which are called up and executed to operate the system. The computer programs $Prg_x$ and stored look-up tables which execute the method in accordance with the invention will preferably also be located here.

Figure 2:
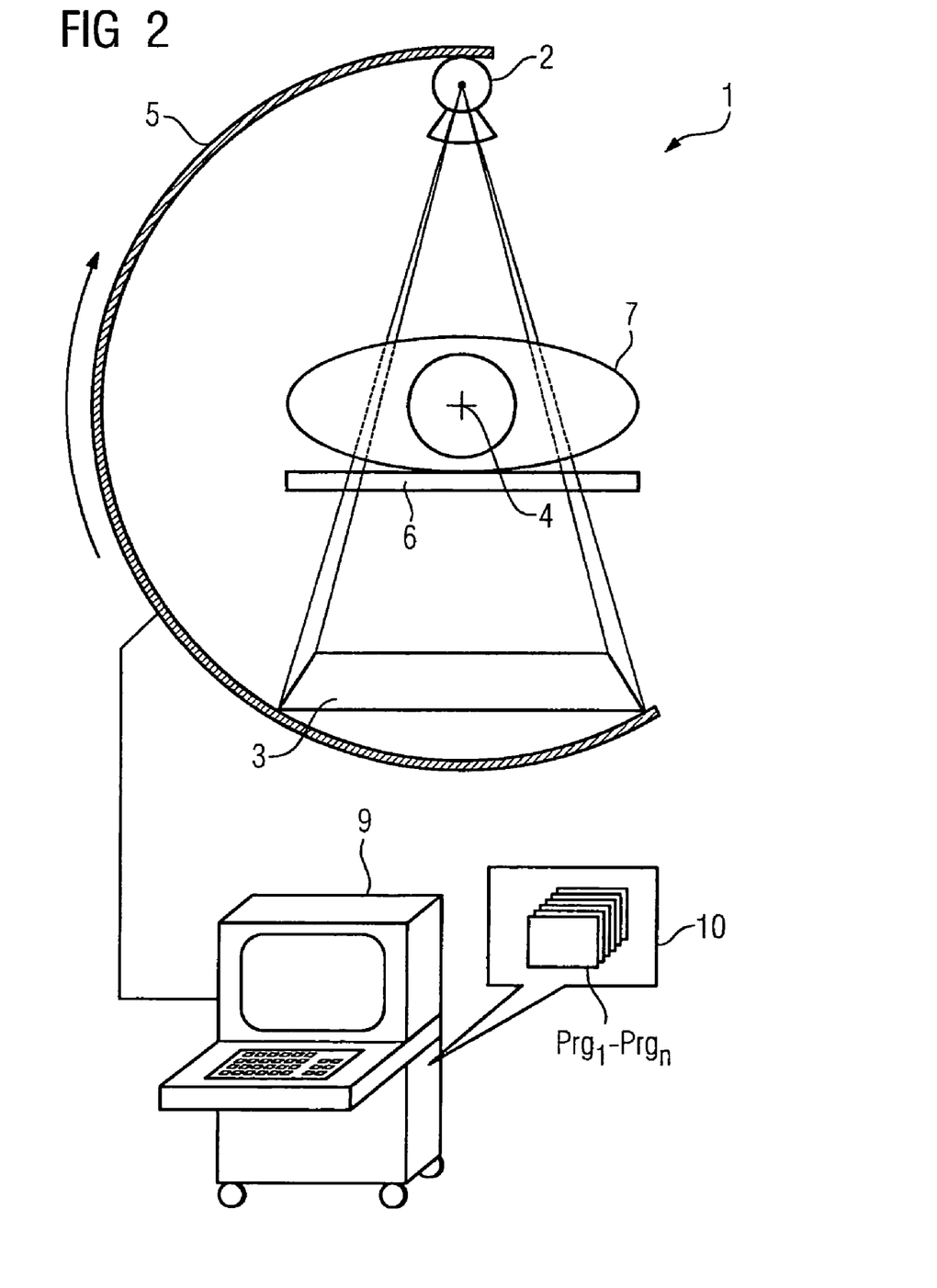
FIG. 2 a schematic diagram of a C-arm device for carrying out the method in accordance with the invention.

The preferred form of embodiment of an X-ray tomography system, for which the method in accordance with the invention described here is used, is shown in cross-section in FIG. 2. This shows a C-arm CT device 1, which is basically familiar, having on its C-arm 5 an X-ray tube 2, which is arranged opposite a large-area detector 3. Using the C-arm 5, the X-ray tube 2 and detector 3 can be rotated around a patient 7, arranged on the patient table 6 in the radiation field and the system axis 4, whereby tomographic images of the patient can be reconstructed from the detector output data, just as with conventional CT using a gantry. The control, analysis of the detector data and reconstruction of the tomographic views are here again effected in a control and computation unit 9, which has a memory 10 for storing away familiar computer programs, and programs $Prg_1$-$Prg_n$ and data tables in accordance with the invention. C-arm devices of this type are used predominantly for coronary angiography.

Because the detector 3 happens here to be a very large-area one, and because it is virtually impossible to realize the application of collimators such as are used for the reduction of scattered radiation in conventional CT systems with one to multi-row detectors, additional measures are required to suppress computationally the effect of scattered radiation on the image. However, because there is at the same time a need for rapid image construction, and the computing power is limited or expensive, the method in accordance with the invention for scattered radiation correction, which is once again presented and explained below, is proposed.

In order to present the basic idea of the invention, it is necessary first to explain the principle of beam hardening correction. In doing so, the following terms will be used:

$Q_U(E)$: voltage-dependent emission spectrum, $\tau_F(E) = \exp(-\mu_F(E)T)$: transparency of the spectral filter used (e.g. copper), $\eta_D(E)$: spectral response sensitivity of the detector, $W_U(E) = Q_U(E)\tau_F(E)\eta_D(E)/c_U$: effective standardized spectral distribution, $$c_U = \int_0^{eU} Q_U(E)\tau_F(E)\eta_D(E)dE, \Rightarrow \int_0^{eU} W_U(E)dE = 1:$$

standardization factor, and eU: maximum energy of the X-ray spectrum in eV.

For the water correction, the simplifying assumption is made that the attenuation of an X-ray beam in the object (patient) is evoked purely by water equivalent material. Here, "water equivalent" means: the energy-dependence of the mass attenuation coefficient $(\mu/\rho)(E)$ is identical to that of water, and differences are due solely to local density differences.

If one now considers a measurement beam which penetrates through the object, with the coordinate along its path designated by x and the location-dependent linear energy-dependent attenuation coefficient given by $\mu(x,E) = \rho(x)\alpha(x,E)$, then the mass attenuation coefficient $\alpha$ is calculated from:

$$\alpha(x,E) = \mu(x,E)/\rho(x).$$

The projection value for the measurement beam under consideration is then:

$$p_a = -\log\left(\int_0^{eU} \exp\left(-\int \mu(x, E)dx\right)W_U dE\right) = $$
$$-\log\left(\int_0^{eU} \exp\left(-\int \rho(x)\alpha(x, E)dx\right)W_U dE\right)$$

where the index $_a$ is intended to indicate "hardening".

For this purpose, a "water equivalent thickness" $b_U = b_u(p_a)$ is determined as follows: Let $\alpha_w(E)$ be the energy-dependent mass attenuation coefficient of water; the polychromatic logarithmic projection value for a measurement beam which is attenuated along the path length (effective thickness) b in water ($\rho = 1$ g/cm$^3$) is:

$$f_U(b) = -\log\left(\int_0^{eU} \exp(-b\alpha_w(E))W_U dE\right)$$

This function can be calculated in advance for any voltage U, or can also be determined experimentally. It increases monotonically with b and can be inverted, e.g. by inverse interpolation.

It is possible to determine for each measured value $p_a$ an equivalent water thickness $b_U = b_U(p_a) = b$ in such a way that $p_a = f_U(b)$ is true, namely by inversion of the last equation, which gives:

$$b_U = f_U^{-1}(p_a)$$

Using $b_U$ it is then possible to convert to the corresponding projection value, which would have been measured in the ideal case with a monochromatic "spectrum" with photons of one single reference energy $E_0$:

Using $b_U = f_U^{-1}(p_a)$ the hardening-corrected projection value becomes $$p^* = \alpha_W(E_0) b_U = \alpha_W(E_0) f_U^{-1}(p_a) = p_a + \delta a$$

where $$\delta a = \alpha_W(E_0) f_U^{-1}(p_a) - p_a$$

The term $\delta a$ represents the explicit form of the hardening correction term, as used below.

Following this preliminary manipulation, the basic idea of the invention will now be presented.

The following terminology is used:
(y,z): Coordinates on the detector;
$I_o = I_o(y,z)$: "calibration image"=measured "unattenuated" intensity distribution with no object in the beam path;
$I_T = I_T(y,z)$: Measured total intensity distribution, including scattered radiation, with the object in the beam path;
$I_A = I_A(y,z)$: Primary intensity distribution with the object in the beam path, with hardening but without scattered radiation;
$I_S = I_S(y,z)$: Intensity distribution solely for the scattered radiation generated by the object;
$T = I_T/I_o$: Standardized total intensity distribution, including scattered radiation, with the object in the beam path;
$P_a = I_A/I_o$: Standardized primary radiation distribution with hardening but with no scattered radiation;
$S = I_S/I_o$: Standardized scattered radiation distribution.

It should be noted here that only the distributions $I_o$ and $I_T$ or T, as applicable, are from measurements. In order to outline the basic idea, the simplifying assumption is made that S and $P_a$ are also known.

The following applies:

$$T = P_a + S \quad (\#1)$$

CT image reconstruction is effected using the negative of the logarithms of standardized intensity data, commonly called "projection data" and here denoted by the lowercase letter p. It then follows from equation (#1) that:

$$p_T = -\log(P_a + S)$$
$$= -\log(P_a(1 + S/P_a))$$
$$= -\log(P_a) - \log(1 + S/P_a)$$

or briefly:

$$p_T = p_a - \delta s \quad (\#2)$$

where $$\delta s = \log(1 + S/P_a) \quad (\#3)$$

Equation (#3) specifies the scattered radiation correction term which must be added to the projection data, $p_T$, which is distorted by scattered radiation, in order to obtain the projection data $p_a$, now only distorted by hardening:

$$p_a = p_T + \delta s \quad (\#4)$$

The hardening-corrected projection data, to be used for the reconstruction, is denoted by $p^*$. The hardening correction or water correction, as applicable, converts $p_a$ to $p^*$ as follows:

$$p^* = p_a + \delta a \quad (\#5),$$

in which $\delta a$ is the hardening correction term indicated above for the beam hardening correction.

If one wishes to formulate the scattered radiation correction as an "amplification" of the hardening correction, it then follows from equations (#4) and (#5) that $$p^* = p_T + \delta a + \delta s$$

$$p^* = p_T + \rho \cdot \delta a \quad (\#6)$$

with the "amplification factor"

$$\rho = 1 + \delta s / \delta a$$

$$\rho = 1 + 1/\delta a \cdot \log(1 + S/P_a) \quad (\#6a)$$

One can see that all the quantities in the preceding equations are location-dependent, i.e. are functions of the location coordinates (y,z) on the detector. This applies in particular for the "amplification factor" $\rho = \rho(y,z)$ in equation (#6a).

An essential point recognized by the invention is that the two terms in equation (#6a), the hardening term $\delta a(y,z)$ and the scattered radiation term $\delta s(y,z)$, have a similar spatial characteristic. For example, if we look at the graph of the two correction terms for a scan of a cylinder, they both initially follow a very flat course out from the middle, and then fall off more steeply towards the edge.

Figure 3:
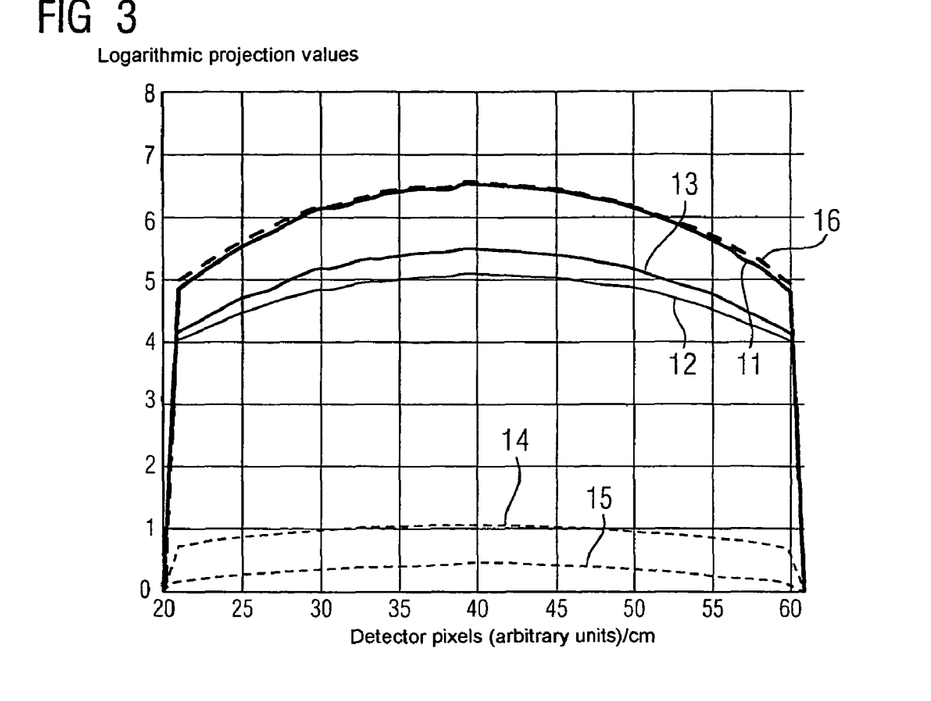
FIG. 3 a comparison of the ideal projection data corrected using the method in accordance with the invention, at a projection angle of 0°.
Figure 4:
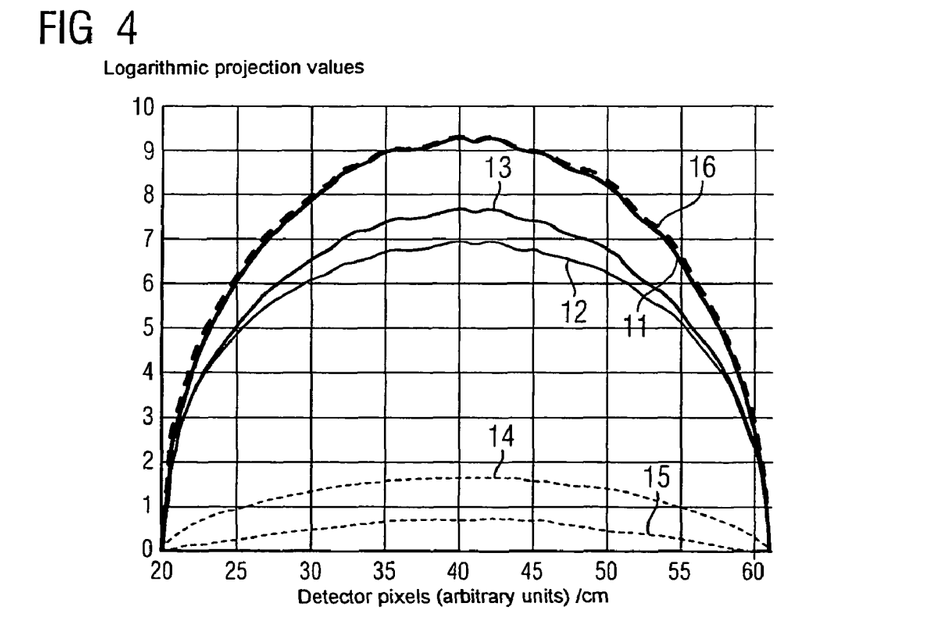
FIG. 4 a comparison of the ideal projection data corrected using the method in accordance with the invention, at a projection angle of 90°.

This characteristic is illustrated in FIGS. 3 and 4 for two different projection angles. FIG. 3 shows the influence of beam hardening correction and scattered radiation correction for a projection angle of 0° for an elliptical phantom, where it should be remarked that, as shown in FIG. 2, for a projection angle of 0° the cone of the beam does not completely envelop the phantom or patient, as applicable.

Along the abscissa are plotted the detector pixels of a central image row, in arbitrary units, while the ordinate scale is the negative of the logarithms of the projection values. Curve 11 shows the graph of error-free projection data, with exact hardening and scattered radiation correction. Curve 12 shows the measured projection values, with no beam hardening correction and no scattered radiation correction, while curve 13 shows the projection data with no scattered radiation portion but with beam hardening correction. Accordingly, difference curves are shown below, curve 14 showing the beam hardening effect alone, and curve 15 containing exclusively the scattered radiation portion.

FIG. 4 illustrates the same, but for a projection angle of 90°, where it is here possible to recognize from the fall-off at the sides of the curve that from the side the beam cone envelops the phantom completely. The reference marks correspond to those used in FIG. 3.

Because the most marked effect on the reconstructed image, the cupping, is determined by the large projection values, i.e. the measurement beams with the greatest attenuation in the object, it is possible to replace $\rho$ in equation (#6a) by a suitable mean value in the region of pixels in the center of the image, or of pixels with the maximum projection value, as appropriate.

If we write $\rho=\rho_o$ for this representative constant, then the exact equation (#6) is replaced by the approximation $$p^*_o = p_T + \rho_o \cdot \delta a \tag{#7a}$$

This then means that the scattered radiation correction can be replaced by amplification of the beam hardening correction term $\delta a$ by a factor $\rho_o$, making it possible to save demanding computational steps.

An improvement in accuracy can be achieved without significant increase in the computation time if, instead of a global amplification factor, a specific amplification factor $\rho_o = \rho_o(z)$ is introduced for each row z in the projection image, this remaining constant for each pixel within the row.

It has been found that for a typical object with an elliptical cross-section the correction method in accordance with equation (#7a) falls off too little towards the edge of the object, leading to a distortive brightening, i.e. although the cupping is reduced a wide bright annulus is produced around the edge of the object.

In order to counteract this effect, one can modify the scattered radiation correction term $\delta s_o = (\rho_o - 1) \cdot \delta a$ in equation (#7a) by multiplying it with a suitable shaping function h(y,z), which has a value range lying between 0 and 1 and which falls off to 0 towards the edge of the object. For this purpose it is possible to use, for example, the projection function $p_T$ itself, standardized and possibly also smoothed. In the notation this is represented by an overscore:

$$h(y,z) = \overline{p_T}(y,z)/\max(\overline{p_T})$$

$$\rho' = \rho_0 - 1$$

$$p^*_1(y,z) = p_T(y,z) + (1+\rho'_1 h(y,z))\delta a(y,z) \tag{#7b}$$

This does again increase the computational effort somewhat, and speed is lost, because by comparison with the algorithm (#7a) there is for each pixel at least an extra addition, a memory access and a multiplication. However, this modified algorithm once again requires no antilogarithms and logarithms to be determined, and is therefore still faster than the familiar algorithm for scattered radiation correction, which is performed on the measured intensities and not on the projection data.

A further improvement in the correction can be achieved by reducing the density excess at the edge of the object, for example the density excess at the edge of an object is really significantly reduced by a generalization of the approach in equation (#7b). For this purpose the approach in (#7b) can be generalized to amplify the fall-off of the shaping function by raising it to a power with an exponent N>=1. The following then applies:

$$h^N(y,z) = [h(y,z)]^N$$

and $$p^*_1(y,z) = p_T(y,z) + (1+\rho'_1 h^N(y,z))\delta a(y,z) \tag{#7c}$$

As mentioned above, in presenting the basic idea of the invention the simplifying assumption was made, for the purpose of estimating $\rho_o$, that S and $P_a$ are known, at least for representative pixels. In equations (#3) and (#6a) one can see that the only input is the ratio $S/P_a$. This can be estimated with the help of an S/P table database. However, the lookup in the S/P table assumes a knowledge of the equivalent water thickness (path length). This is then calculated from the logarithm of the projection value $p_a = -\log(P_a)$, using an algorithm which is known per se as part of the water correction.

The retrieval from the S/P database, using the algorithm cited, of the quotient $S/P_a$ required in equation (#6a), is described briefly by $$S/P_a = g(p_a) \tag{#8}$$

This term depends on $p_a$, but $p_a$ is for its part only known after estimation of the ratio $S/P_a$ of scattered to primary. This implicit problem can be solved iteratively. To simplify the notation, in what follows $p_a$ and $p_T$ refer only to scalar values, because for the determination of $\rho_o$ one can restrict oneself to a mean pixel value. The iteration rule for $p_a$ then reads as follows:

$$\text{Start: } p_a^{(0)} = p_T \tag{#9a}$$

$$\text{Iteration } (n \geq 0): p_a^{(n+1)} = p_T + \log(1 + g(p_a^{(n)})) \tag{#9b}$$

In general, two to three iterations suffice.

Because the correction method operates directly on the projection data, it is independent of the exposure geometry, but nevertheless this must be taken into account in creating the S/P database, and in principle any suitable reconstruction algorithm can be used.

Now refer again to FIGS. 3 and 4, in which are shown the results of the scattered radiation correction in accordance with the invention, with the reference mark 16. It can be seen that the differences from the ideal graph of the projection data, in particular at the 90° projection angle, are very small, so that scarcely any loss of quality is to be expected in the image display from this scattered radiation correction, which can be performed with very little computational cost.

In concrete terms, the scattered radiation correction can be carried out as an amplified water correction, using a constant amplification factor for each projection image, thus corresponding to the following work steps:

Initially, the appropriate pre-calculated multi-dimensional S/P table, which still depends on the tube voltage and the air gap and on the exposure parameters such as the array size, antiscatter grid, prefiltering etc. used for data acquisition, is read in.

After this, for each projection image, which consists of logarithms of the data, a global amplification factor $\rho$ is determined as follows:

1. Extract the S/P sub-table which is specific to the tube voltage, and the air gap which may have to be estimated;
2. Reduce the projection image (e.g. by 8×8 downsampling or binning; median or low-pass filtering);
3. Determine the pixel with the maximum projection value and the mean value from, e.g. 5×5 pixels including the maximum;
4. Use this mean value for $p_S$ and by means of an iteration algorithm as shown in equations (#9a, b) calculate an estimate of $p_a$;
5. Determine the hardening correction term $\delta a = \alpha_W(E_0) f_U^{-1}(p_a) - p_a$
6. Determine the amplification factor $\rho$ as in equation (#7b), where value of the term $S/P_a$ is to be determined as implied by equation (#8) using the S/P table.

Then, for each pixel in each projection image, the amplified water correction shown by equation (#6) is applied, using the constant amplification factor $\rho$ previously determined.

A possible variant of this approach consists in using in step 3 not the maximum value but instead the mean value in a so-called "dominant". After this, in the modified step 3, the mean value is calculated for a prescribed dominant, which is a reduced region, generally a prescribed small ROI (=region of interest) in the middle of the detector.

In accordance with the invention, the scattered radiation correction can also take place as an amplified water correction, with a constant amplification factor for each image row of each projection image. Here, instead of a global amplification factor a specific amplification factor $\rho=\rho(z)$ is introduced for each row z in the projection image, but this remains constant for each pixel within the row. This modification of the method, which does somewhat increase the computational effort, achieves an improvement in the accuracy. The sequence of program steps for each projection image then changes as follows:

First, as a general preparation, for each projection image of logarithmic data:

an S/P sub-table is extracted which is specific to the tube voltage and possibly to the air-gap which must be estimated;

the projection image is reduced, e.g. by 4×4 downsampling or binning and median or low-pass filtering;

This is now followed by determination of the row-dependent amplification factor $\rho(z)$, with: the determination for each row z' in the reduced projection image of an amplification factor $\rho(z')$ by the steps:

Determination of the pixel with the maximum projection value and determination of the mean value of several pixels including the maximum; (alternatively, analogous to the variant 5.2: mean value across 5 cm in the region of the middle of the row)

Use this mean value for $p_S$ and by means of an iteration algorithm as shown in equations (#9a,b) calculate an estimate of $p_a$;

Determine the hardening correction term $\delta a=\delta a(z')$ from $\delta a = a_W(E_0) f_U^{-1}(p_a) - p_a$ Determine the amplification factor $\rho=\rho(z')$ as in equation (#7b), where value of the term $S/P_a$ is to be determined as implied by equation (#8) using the S/P table.

The amplification factor $\rho(z')$ determined on the reduced row grid is now expanded onto the original fine grid by linear interpolation; beforehand, smoothing can be carried out by 1-dimensional convolution.

Finally, the water correction is performed for each row z of the projection image, using the amplification factor $\rho(z)$.

In sum, therefore, the invention makes available a scattered radiation correction which is based on the hardening correction and is applied to the logarithms of the projection data. This means that it is no longer necessary, before and for the purpose of scattered radiation correction, to take the antilogarithms of the CT data which is being used and then, after the correction has been effected, to take the logarithms again, thus enabling a not inconsiderable computational effort to be saved.

It goes without saying that the characteristics of the invention cited above can be used not only in the combination described in each case, but also in other combinations, or separately, without going outside the bounds of the invention.

What is claimed is:

1. A method for providing scattered radiation correction in a computed tomography system having a radiation source and a large-area multi-row detector, comprising:

emitting radiation from the radiation source;

scanning an object from a plurality of projection angles by the radiation;

measuring an attenuation of the radiation;

generating initial projection data $p_T$ for the scanning using the measured attenuation;

applying first and second functions in a single step to the projection data to provide corrected projection data p* and reconstructing a tomographic view by postprocessing the corrected projection data wherein the first function provides a beam hardening correction and the second function provides a scattered radiation correction, wherein:

the corrected projection data $p^* = p_T + \rho \cdot \delta_a$ with $\rho = 1 + 1/\delta_a \log(1+S/P_a)$ thereby combining the first and second functions to effect both the beam hardening correction and the scattered radiation correction, and wherein $\delta_a$ is a hardening correction term that effects the beam hardening correction, S is a standardized scattered radiation distribution, and $P_a$ is a standardized primary radiation with hardening but without scattered radiation, and $\rho$ is an amplification factor for a radiation scatter correction.

2. The method as claimed in claim 1, wherein the attenuation of the radiation equals $I_T/I_0$, wherein:

$I_T$ is a measured total radiation intensity distribution including scattered radiation with the object in a radiation beam path, and $I_0$ is a measured unattenuated radiation intensity distribution with no object in the radiation beam path.

3. The method as claimed in claim 2, wherein the initial projection data $p_T$ is generated by equation $p_T = \log I_T/I_0$.

4. The method as claimed in claim 1, wherein the ratio of the standardized scattered radiation distribution S to the standardized primary radiation distribution with hardening but without scattered radiation $P_a$ is estimated for a representative pixel.

5. The method as claimed in claim 1, wherein the ratio of the standardized scattered radiation distribution S to the standardized primary radiation distribution with hardening but without scattered radiation $P_a$ is taken from a simulation data for a phantom with a similar shape, size and structure to the object.

6. The method as claimed in claim 1, wherein the ratio of the standardized scattered radiation distribution S to the standardized primary radiation distribution with hardening but without scattered radiation $P_a$ is approximated by an iterative method.

7. The method as claimed in claim 1, wherein the scattered radiation correction is dependent on a location relative to the detector.

8. The method as claimed in claim 1, wherein the scattered radiation correction is dependent on a row of the detector.

9. The method as claimed in claim 1, wherein the scattered radiation correction is dependent on the projection angle.

10. A computed tomography system for scanning an object in a medical procedure, comprising:

a radiation source that emits a radiation;

a large-area multi-row detector that detects the radiation scanning the object;

a measuring device that measures a value for an attenuation of the radiation; and a control and computation unit that is configured to:

generate projection data for the scanning using the measured value for the attenuation of the radiation, and apply first and second functions in a single step to the projection data to provide corrected projection data p* and reconstruct a tomographic view by postprocessing the corrected projection data wherein the first function provides a beam hardening correction and the second function provides a scattered radiation correction, wherein:

the corrected projection data $p^* = p_T + \rho \cdot \delta_a$ with $\rho = 1 + 1/\delta_a \log(1+S/P_a)$ thereby combining the first and second functions to effect both the beam hardening correction and the scattered radiation correction, and wherein $\delta_a$ is a hardening correction term that effects the beam hardening correction, S is a standardized scattered radiation distribution, $P_a$ is a standardized primary radiation with hardening but without scattered radiation, and $\rho$ is an amplification factor for a radiation scatter correction.

11. The computed tomography system as claimed in claim 10, wherein the attenuation of the radiation is a standardized total radiation intensity distribution including scattered radiation with the object in a beam path.

* * * * *